United States Patent [19]
Akita et al.

[11] Patent Number: 5,472,473
[45] Date of Patent: Dec. 5, 1995

[54] METHOD FOR TREATING LIQUID WASTES FROM LIVESTOCK

[76] Inventors: Tadahiko Akita, 17-4, Nakamura-3-chome, Nerima-ku, Tokyo; Morio Shiina, 2505, Shirasu-machi Yokote, Kitakoma-gun, Yamanashi-ken, both of Japan

[21] Appl. No.: 211,238

[22] PCT Filed: Jul. 20, 1993

[86] PCT No.: PCT/JP93/01012
§ 371 Date: Mar. 29, 1994
§ 102(e) Date: Mar. 29, 1994

[87] PCT Pub. No.: WO94/03411
PCT Pub. Date: Feb. 17, 1994

[30] Foreign Application Priority Data

Aug. 7, 1992 [JP] Japan ..................................... 4-231633

[51] Int. Cl.[6] .................................................. C05F 11/08
[52] U.S. Cl. .................................. 71/9; 71/6; 71/8
[58] Field of Search .......................................... 71/6, 8, 9

[56] References Cited

U.S. PATENT DOCUMENTS

| | | | |
|---|---|---|---|
| 71,689 | 12/1867 | Bitner | 71/9 |
| 3,761,237 | 9/1973 | Jeffreys | 71/9 |
| 4,486,216 | 12/1984 | von Raven et al. | 71/9 |
| 4,559,073 | 12/1985 | Minato et al. | 71/9 |
| 5,192,428 | 3/1993 | Lindstrom | 71/9 |

FOREIGN PATENT DOCUMENTS

| | | | |
|---|---|---|---|
| 145113 | 12/1952 | Australia | 71/9 |
| 541184 | 11/1992 | European Pat. Off. | 71/9 |
| 3409019 | 9/1985 | Germany | 71/9 |
| 3639993 | 7/1987 | Germany | 71/9 |
| 21780 | 1/1987 | Japan | 71/8 |

*Primary Examiner*—Wayne Langel
*Attorney, Agent, or Firm*—Oblon, Spivak, McClelland, Maier, & Neustadt

[57] ABSTRACT

Urine discharged from domestic animals is stored in a reservoir, filtered to separate solid and liquid components, and sent to one or more treating tanks. Various rocks and soil humus are added to the treatment tank, which is aerated to acceleratedly produce humus and to cause proliferation of soil microorganisms in the wastes. The rocks are added to serve as catalysts for the bioreactions. As a result, the soil microorganisms that contribute to humus production are markedly activated, and the liquid waste is quickly and efficiently detoxified and rendered odorless. The resultant aqueous solution contains high concentrations of activated soil microorganisms and their metabolic products which can be used as an agricultural material.

4 Claims, 3 Drawing Sheets

METHOD FOR TREATING LIQUID WASTES FROM LIVESTOCK

FIELD OF THE INVENTION

The present invention relates to a method for treating wastes from livestock such as urine, and specifically to a waste treatment method that produces an aqueous solution containing a high density of activated soil microorganisms and their metabolic products which can be utilized as useful agricultural material.

BACKGROUND OF THE INVENTION

Growth in the livestock and dairy industries has made it necessary to process increasingly large quantities of animal wastes, which cause nasty and offensive odors resulting in enviromental pollution. The offensive odors and other environmental pollution generated in barns also face practical limitations on where dairy and livestock farms can be located, since urine emits especially offensive odors and contaminates water systems. The farming industry incurs large operating costs in treating such waste on account of the large-scale facilities and complicated processing involved. Moreover, it takes a fairly long time to reduce the offensive odors caused by urine to a tolerable level.

Wastes or excretions from domestic animals, such as diary cattle, beef cattle, swine, sheep and the like, contain organic materials, when properly treated, that can benefitably be reutilized for agricultural purposes. Wastes from domestic animals have traditionally been turned into compost and used as a fertilizer, but composting requires much time and labor. Many effective techniques have been developed to reuse solid wastes for fertilizer and compost.

In traditional composting, solid wastes, after adjusting their water content, are cured in air for an extended period with periodic stirring. At that time, microorganisms in soil decompose this mixture into humus, thus transforming it into compost. This natural process has detrimental drawbacks, such as requiring a long curing time and much labor. Another disadvantage is the difficulty in securing a physically and chemically stable product. Given limitations in the availability of labor, large-scale facilities and lands, traditional composting can not be applied for today's large-scale livestock and dairy farms, where large quantities of wastes are excreted day-by-day.

Among various forms of animal wastes, urine is the most difficult to treat due to its high ammonia content. In fact, an effective means for treating urine has never been developed until now.

The inventors of the present application have studied recycling methods for treating urine and other liquid wastes more efficiently with suppressing the emission of nasty and offensive odors to convert them to a material that can be reused for various agricultural purposes.

First of all, the present invention is turned its attention to the characteristics of soil. Soil is a source of sustenance for plant and animal lifes, and absorbs the remains of plants and animals after they die. Wastes excreted from animals and plants, their remains, and other organic materials eventually are decomposed into inorganic compounds and synthesize humus. The problems such as puterfaction and offensive odors do not occur during the decomposition in soil. Soil that contains a large quantity of humus is generally capable of yielding large crops without the use of additional fertilizers. Moreover, humus makes toxic metallic ions and nonmetallic substances harmless, and helps to preserve the natural ecological balance while preventing the proliferation of harmful insects.

In accordance with the present invention, considering how soil breaks down organic wastes, a new method for treating wastes has been developed in a manner facilitated by incorporating this natural process.

Organic materials in soil synthesize humus in the processes of chemical reactions, in which processes soil microorganisms play a vital role. FIG. 1 shows the mechanism of producing humus. In one of the chemical reactions, microorganisms decompose organic materials into water and inorganic substances, thereby reducing their molecular weights. The resultant products of this decomposing reaction are useless substances and further generates the offensive odors usually associated with ammonia and methane. The products are also incapable of preventing the proliferation of harmful bacteria and insects.

On the other hand, soil organics can be composed of carbohydrates, lignin, and proteins from organic substances. Microorganisms consume carbohydrates and lignin as a source of energy, and in turn secrete phenolic compounds and other metabolic by-products. Soil microorganisms also obtain nutrition by decomposing proteins into amino acids and peptides. Humus is eventually synthesized through these chemical reactions.

Humus—which consists of humin, humic acid, and fulvenic acid—has a natural purification function. The purification process quickly changes animal and plant wastes into soil humus and high-quality water, thus resulting to control the growth of miscellaneous bacteria, to prevent the decay thereof, and to eliminate offensive odors. Minerals and water exhibit essential function for promoting the metabolic activities of the microorganisms in soil to accelerate the production of humus. The inorganic substances in soil consist mainly of the clay and minerals found in the particular area. These minerals serve as an activator for the microorganisms' metabolism. Moreover, water in soil differs in composition from ordinary "pure" water by extensively dissolving various mineral particles. The water in soil has a favorable effect on crops and microorganisms.

In summary, minerals and water having minerals dissolved therein are the essential materials for promoting the metabolic activities of soil microorganisms and producing humus from organic substances in the soil. The earth's ecosystems have been maintained over 3.5 billion years by the vital participation of microorganisms.

Laid-Open-Publication of Japanese Patent Application No. 4-238887 discloses a method for producing highly cured compost on an industrial scale. According to the prior art, the compost is produced from solid organic wastes, such as animal wastes, as the starting material. In the method disclosed therein, to accelerate the production of humus, a substance for activating soil microorganisms is added to solid wastes (mainly excrement) from domestic animals. Specifically, water content in solid wastes as the starting material is controlled to 60%–70%. Then, seed compost and silicate particles derived from andesite or rhyolite are added to activate the metabolic functions of the soil microorganisms, specifically in the form of facultative anaerobes, or a mixture of facultative anaerobes and aerobic bacteria. In short, the starting material is mixed uniformly with agents that promote humus production. The mixture is stirred periodically during the curing period. By so processing, well-cured compost is obtained in a very short period of time.

Further, Laid-Open-Publication of Japanese Patent Application No. 4-265286 discloses a method for converting the well-cured compost produced as described above into liquid form. That is, the well-cured compost, which is rich in soil microorganisms, is dissolved in water in the presence of granite, rhyolite, or basalt as an active ingredient. The mixture is then aerated to activate the microorganisms, obtained the obtained mixture thereby obtained being an aqueous solution concentrated with soil microorganisms and their metabolic by-products. The aqueous solution is then extracted from the mixture by the filtration to remove solid components, thus obtaining a liquid compost which can be applied together with solid compost to farmlands or other greenery areas and may be used as a seed compost for the source of bacteria of materials to be composted.

DISCRIPTION OF THE INVENTION

Basically, the present invention is intended to improve the working environment in barns and to eliminate various problems generally experienced on livestock and dairy farms, by the treatment of liquid wastes such as urine from domestic animals effectively with the aid of soil microorganisms, whose metabolic activities are sustained through the functions of minerals and high-quality water.

Therefore, an object of the present invention is to provide optimal conditions in a natural bioreactor system so as to rapidly deodorize and detoxify liquid animal wastes, which is very difficult to treat by conventional methods.

Another object of the present invention is to produce from liquid wasets of domestic animals, at low cost, large quantities of aqueous materials for agricultural use which contains a high concentration of soil microorganisms and their metabolic products.

Yet another object of the present invention is to improve beforehand the wastes discharged from the animals, by supplying qualified drinking water for domestic animals so as to fairly reduce the operation load of the treatment equipment.

To achieve the above-mentioned objects, the present invention relates to a method for treating liquid wastes of domestic animals, which comprises mixing the liquid wastes with soil humus, bioreacting the mixture with aeration in the presense of rocks and soil humus in order to accelerate the metabolic activities of the microorganisms, and extracting an aqueous solution containing activated soil microorganisms and their metabolic products from the mixture.

More specifically, the present invention relates to a method for treating liquid wastes of domestic animals which comprises raising the domestic animals using as their drinking water dissolved useful minerals from the rocks and soil microorganisms prepared by mixing in water a plurality of igneous rocks selected from andesite, basalt, granite, rhyolite, and peridotite, and soil humus with aeration, collecting liquid wastes from the domestic animals using said drinking water, and mixing in said liquid wastes a plurality of igneous rocks selected from andesite, basalt, granite, rhyolite, and peridotite, and soil humus for activating the soil microorganisms to convert into an aqueous solution containing activated microorganisms and their metabolic products.

DETAILED DESCRIPTION OF THE INVENTION

Figure 1:
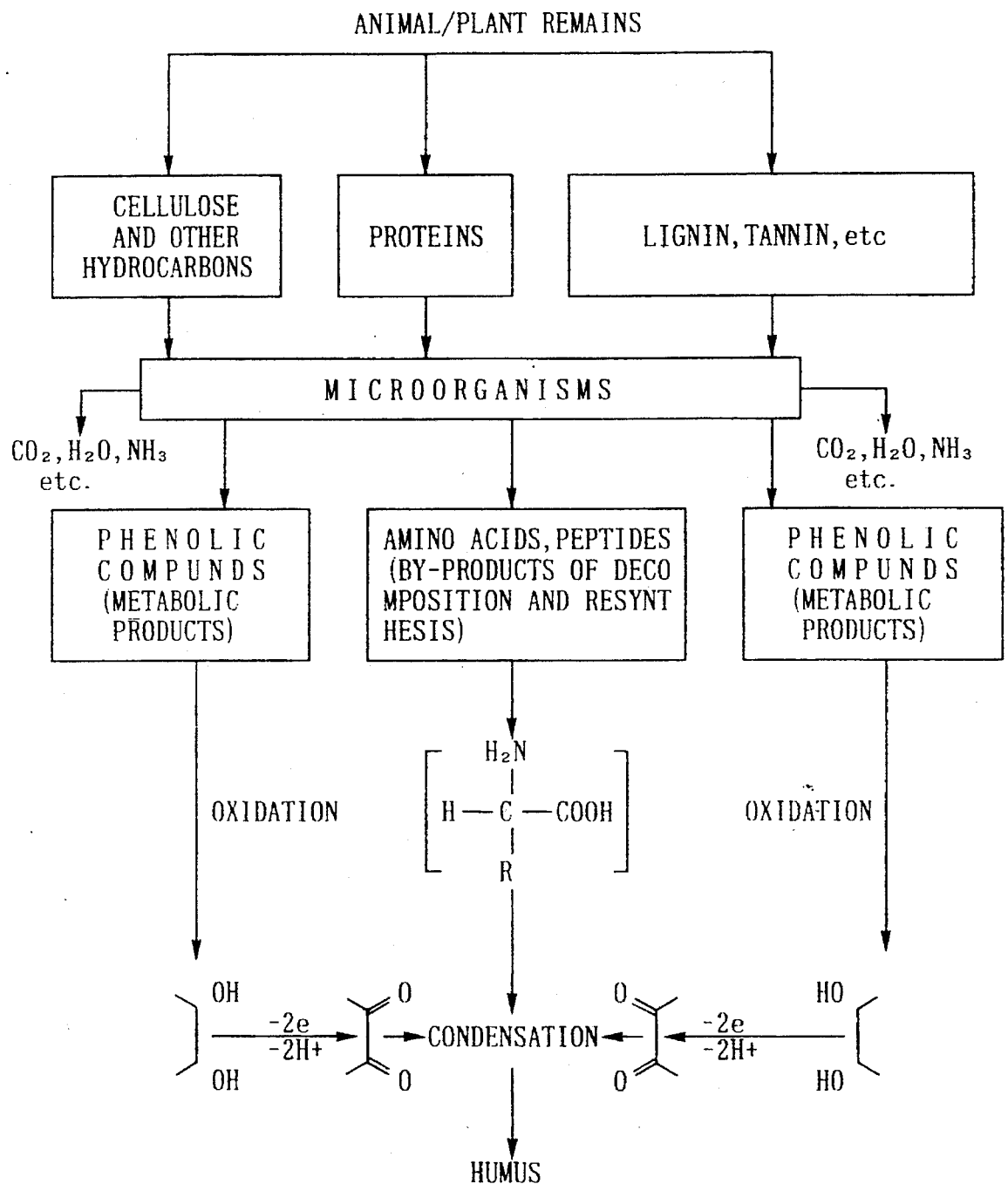
FIG. 1 is a flow diagram of reaction systems to produce humus.

A starting material to be treated according to the present invention, is liquid wastes or excretions from livestock, such as diary cattle, beef cattle, swine, sheep and the like. The liquid component in the starting material is, in the first place, separated from insoluble solid ingredients. Then, the organic substances contained in the liquid is caused to react to produce humus by means of a bioreaction in the presence of soil microorganism. Igneous rocks and soil humus are added to the liquid so as to accelerate the production of humus. Rocks to be used as catalysts of the bioreaction are andesite, basalt, granite, rhyolite, and periodotite, and must be free from excessive weathering. Preferably, two or more kinds of rocks are combined to render the culture medium more hospitable to soil microorganisms. Although urine discharged from domestic animals inherently contains the above useful microorganisms, in the method of the present invention, the concentration of soil microorganisms is intentional increased in the bioreactor system so as to accelerate the mechanism for humus production.

By causing the reaction promptly and efficiently, the organic materials consisting mainly of animal urine are, on the one hand, quickly and thoroughly decomposed into carbon dioxide, water, nitrates, nitrogen gas, and on the other hand are converted to produce humus, thereby completely removing offensive and nasty odors, exterminating harmful bacteria such as colon bacilli, and producing as the resulting product an aqueous solution that contains high concentrations of useful soil microorganisms, their metabolic products and useful minerals. By this bioreaction, at least 95% of the carbon and nitrogen are removed from the starting material.

Kinds of microorganisms used in this method are not specified due to the fact that, although there are estimated to exist several hundreds of million kinds of microorganism species, a extremely small portion of which have now been classified and revealed their functions. For this reason, it can not be actually specified which particular microorganisms are effective as the catalyzer in the bioreactor of this invention. Therefore, it is impossible to identify which microorganisms are really involved in the producing humus from organic materials. Moreover, the metabolic activities of these microorganisms may either become aerobic or become anaerobic, depending on the conditions under which they are present. Humus thus must be produced as a result of total functions of various microorganisms without specifying which are useful species to produce humus. The most important consideration is to prepare as much as possible the essential and fundamental conditions to promote the growth of microorganisms and production of humus in soil For this purpose, igneous rocks found in the earth's crust are used in the bioreactor system in order to facilitate to stimulate the maximum growth of microorganisms and their metabolic activities. Minerals in the rocks have a function of a catalyst for producing humus by means of the actions of these microorganisms. These minerals also can be changed to available forms for plants by the metabolism products of the microorganisms. As a result, the substance produced in accordance with the method of the present invention is turned into a material that is rich in mineral nutrients suitable for use as an agricultural fertilizer.

As for the minerals, it is preferable not to use a specific rock or clay mineral having a particular metallic element. Various rocks and minerals with which the microorganisms have come in contact over the past 3.5 billion years are to be generally used. The earth's crusts consist mainly of andesite and granite. Basalt, rhyolite, or periodotite should be used in the whole processes of the bioreactions in addition to the above two representative rocks.

In the bioreactions of the present invention, soil humus and minerals are used for acceleration of the growth of the soil microorganisms. The soil humus used in the present invention is either untreated or a substance as prepared according to the above-mentioned Laid-Open Publication of Japanese Patent Application No. 4-238887 in the form of pellets or balls.

To make the bioreactions proceed smoothly and efficiently, it is preferable to improve beforehand and the urine excreted by the domestic animals. This can be done by conditioning the water for the drink of the animals. One approach is to mix the water in suitable proportions in a tank with soil humus and the above-described rocks, and to aerate this mixture. Another approach is to mix in water with a small amount of the liquid compost prepared by the method disclosed by Laid-Open-Publication of Japanese Patent Application No. 4-265286. The drinking water is processed in such a way so to contain useful minerals and soil microorganisms. Such drinking water promotes the health of the domestic animals, improves the environment around barns, and reduces offensive odors emitted from their wastes, while further reducing the concentration of colon bacilli and other toxic bacteria. Thus, the pretreatment of drinking water can reduce the load of treatment required for wastes discharged from the animals and improve the quality of the treated liquid effluent, especially when such effluent is to be used for agricultural purposes.

DETAILED DESCRIPTION OF THE INVENTION AND SPECIFIC EMBODIMENT

The method of the present invention for treating liquid animal wastes is now described in detail.

Excretions from livestock or domestic animals are stored in a reservoir. A liquid component is extracted by filtration therefrom to remove solid components, where necessary. The liquid wastes are then introduced into a reaction tank to which rocks and soil humus have been added to cause bioreactions with an appropriate aeration. The purpose of the bioreaction is to change the organic substances in the wastes into humus caused by the presence of microorganisms in the soil humus and liquid wastes. The rocks are added as a catalyzer to the tank to promote as a the bioreactions, and aeration helps to create optimal conditions for the proliferation of the microorganisms.

Although one treatment tank is sufficient to accomplish the reactions, it is better to use two or more tanks to improve the treatment efficiency and to accelerate the reaction, by shifting the supernatant liquid of one tank to another depending upon the developments of the reactions. A certain quantity of the supernatant liquid from the final treatment tank is stored to the product tank as a final product in the form of an aqueous solution. A part of the supernatant can be recycled back to the first treatment tank, thus accelerating the reactions in the first tank.

In the course of the bioreactions, the soil microorganisms are proliferated by the undecomposed organic nutrients in the starting material and the organic nutrients are decomposed in part into carbon dioxide and nitrogen gas, which are released from the system. The microorganisms also convert the remaining materials into humus through their metabolic activities. After the organic materials in the starting material have been completely decomposed, the aqueous solution becomes odorless and glossy light brown in color.

By the above-mentioned processes, urine-based animal wastes, which are difficult to treat by conventional methods, can be recycled to a useful agricultural liquid materials which contain a high proportion of activated soil microorganisms, humus and their metabolic by-products, and dissolve minerals in the rocks. No offensive odors or other pollutants are emitted during the course of the reactions. When applied to agricultural or other lands, this liquid improves soil conditions and accelerates crop growth. The liquid can serve as a seed liquid to promote the fermentation of compost, and can also be used to cure livestock feed. This liquid can also be used for the prevention of the decay of organic wastes and as a deodrant for daily wastes. Another application of this liquid is to supplement drinking water for animals. Finally, because the liquid product contains oxidized or condensed phenolic organics, it can be used as bactericide and insecticide to prevent the proliferation of harmful insects..

EXAMPLE 1

Figure 2:
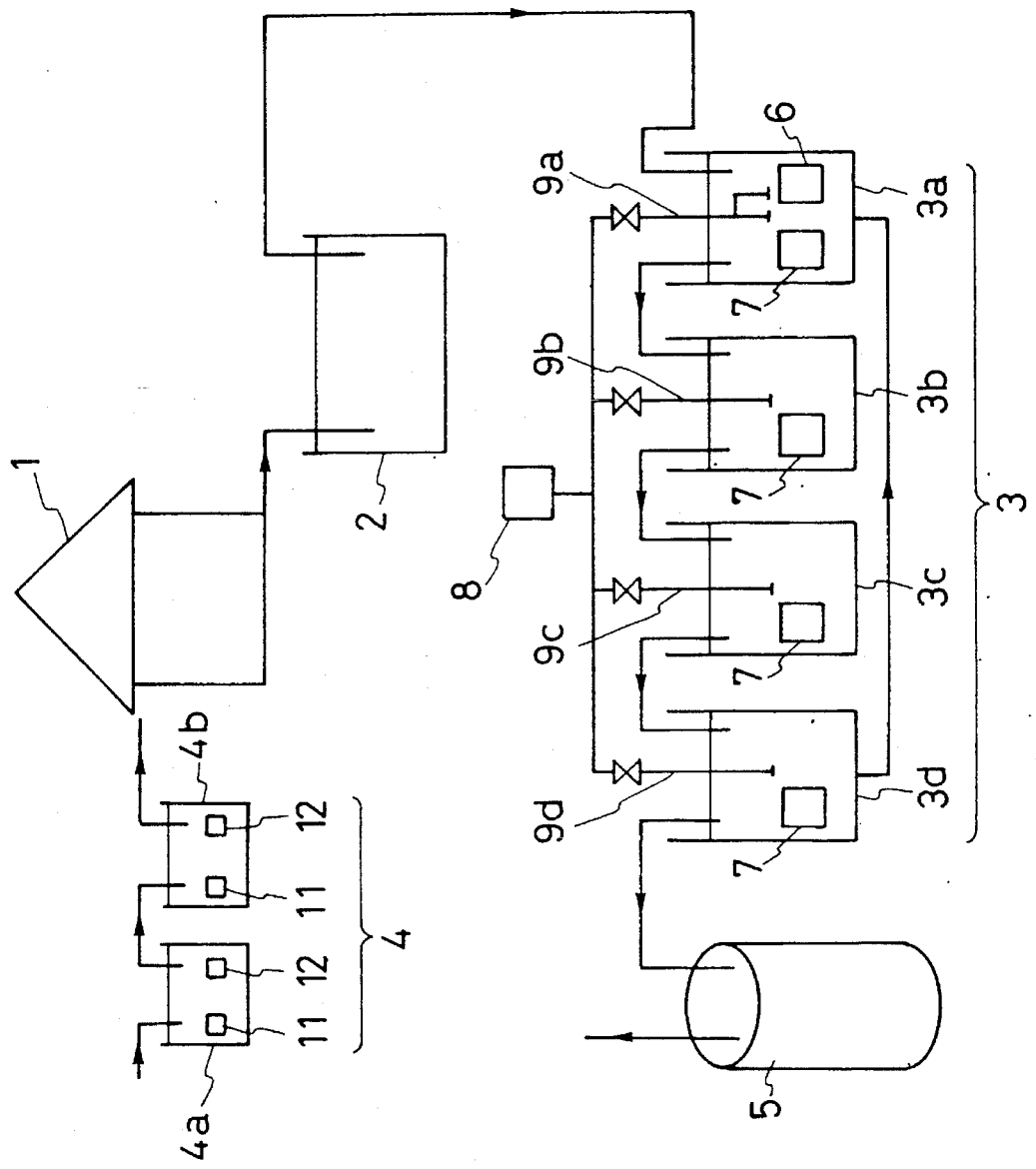
FIG. 2 is a diagrammatic view of an apparatus for treating wastes of the first embodiment.

Illustrated in FIG. 2 is an apparatus for processing liquid wastes discharged from dairy cattle.

Reference numeral 1 denotes a barn in which diary cattle is raised, 2 a urine reservoir, 3 a treating equipment, wherein the treating equipment 3 has four urine treating tanks 3a to 3d. Further, 4 is a drinking water treatment apparatus which has two drinking watertanks 4a and 4b. 5 is a reservoier tank. Of the urine treating tanks 3a to 3d, in the first tank 3a is provided pelletized soil humus 6 and crushed igneous rocks 7. While, in the second to fourth tanks 3a to 3d are provided only crushed igneous rocks 7, but not necessarily the pelletized soil humus. Each of the urine treatment tanks 3a through 3d can be aerated by means of aeration pipes 9a to 9d which are connected to an aeration unit 8. Also, pelletized soil humus 10 and crushed igneous rocks 11 are provided in the drinking water tanks 4a and 4b similar to the urine treatment tank 3a.

The wastewater including urine and cleaning water for the barn 1 is sent by a conveyor from the barn 1 to the urine reservoir 2 installed adjacent to the barn 1. The wastewater as the starting material is pumped up from the urine reservoir 2 for sending to the first tank 3a. In the first tank 3a, the wastewater is aerated by means of the aeration unit 8 to cause the bioreactions during approximately 120 hours. Since the first tank 3a holds pelletized soil humus 6 and crushed igneous rock 7, bioreaction is brought about in an accelerated manner to the starting material of the wastewater by the functions of humus and other useful minerals derived from pelletized soil humus 6 and crushed igneous rocks 7, thus promptly decreasing offensive and nasty odors. Although the optimal ratio varies depending upon the urine content in the starting material, approximately 10 kg of humus and 500 kg of rock should be added to the tank 3a having a capacity of 8,000 liters for the acceleration of the reaction. After the bioreaction progressed to a considerable degree in the first tank 3a, the supernatant liquor is sent to the second tank 3b wherein the bioreaction proceeds for 120 hours. In similar fashion, the supernatant liquor is sent to the third tank 3c and to the fourth tanks 3d in order. The bioreaction is allowed to proceed for 120 hours in each of these tanks. The supernatant liquid in the fourth tank 3d is taken out as the final liquid product to the reservoier tank 5. The thus obtained liquid is an odorless and glossy brown aqueous solution which is rich in activated soil microorganisms and their metabolic by-products. The aqueous solution is free of ammonia, nitrous compounds, and colon bacilli. A part of the solution can be recycled from the fourth tank 3d back to the first tank 3a, thereby improving the efficiency of the bioreaction.

When the drinking water is used as a mixture of water and the aqueous solution in the drinking water tanks 4a and 4b pretreated with soil microorganisms and minerals, the diary cattle discharges urine which contains a high concentration of soil microorganisms and minerals. By doing so, the offensive odors and the treatment load are further eliminated. The results of microorganisms and chemical analysis of the liquid obtained from the treatment of urine discharged from Holstein cattle are shown in Table 1 and 2.

Table 1 gives the number of bacteria species changed stage by stage in the treatment process to produce the aqueous solution containing high proportions of activated microorganisms and their metabolic by-products. Table 2 gives the chemical analysis results at each stage.

TABLE 1

| bacteria species | starting liquid | intermediate tanks | final tanks |
| --- | --- | --- | --- |
| facultative anaerobes | 0 | 0 | 0 |
| wild yeast fungi | $3.8 \times 10^3$ | $7.0 \times 10^3$ | $1.9 \times 10^3$ |
| filamentous fungi | $1.7 \times 10^2$ | 7.0 | 0 |
| Actinomyces | $8.0 \times 10^5$ | $2.9 \times 10^5$ | $1.6 \times 10^8$ |
| colon bacilli | 0 | 0 | 0 |

(Note)

Unit: Number of bacteria/ml
Culture Media Used

| Facultative Anaerobes: | GYP Agar |
| --- | --- |
| Wild Yeast Fungi: | YM Agar |
| Filamentous Fungi: | PD Agar |
| Actinomyces: | Wackman Agar |
| Colon Bacilli: | Denkisyfleet Agar |

TABLE 2

|  | pH | T'N | $P_2O_5$ | $K_2O$ |
| --- | --- | --- | --- | --- |
| starting liquid | 8.31 | 0.679% | 0.057% | 1.355% |
| intermediate tanks | 8.33 | 0.023% | 0.12% | 0.313% |
| final tank | 8.29 | 0.009% | 0.000% | 0.243% |

As is apparent from the tables, the concentration of Actinomyces at the final tank was very high of $10^8$/ml, and nitrogen treatment efficiency was nearly 100%.

EXAMPLE 2

Figure 3:
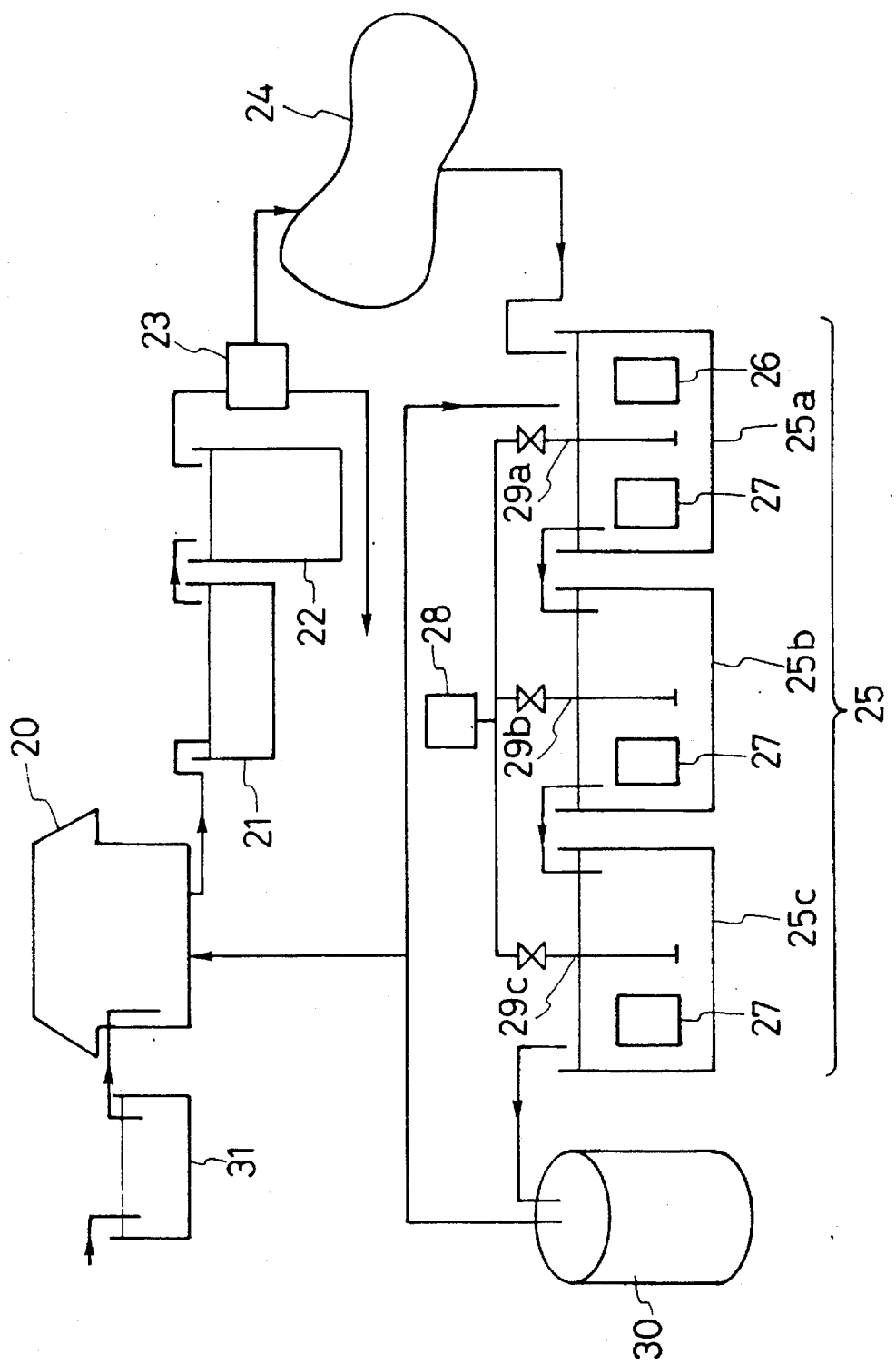
FIG. 3 is a diagrammatic view of an apparatus for treating wastes of the second embodiment.

FIG. 3 illustrates a construction such that urine discharged from pigs raised in a swinery is processed.

In FIG. 3, 20 denotes a swinery barn in which the pigs are raised, a waste pit 21 is provided in the swinery barn 20. The wastewater, mainly consisting of urine discharged from the pigs, is sent to a waste reservoir 22. The wastewater is further passed through a filter 23 for separating the solid and liquid components of the waste sent from the reservoir 22, and then supplying a pond 24 for storing urine to be treated. The solid component of the wastes removed by the filter 23 is sent to the compost-producing system. The liquid component, consisting mainly of urine, is sent to a urine treatment system 25 to convert into an aqueous solution containing a high concentration of activated microorganisms and their metabolic by-products. The treatment system 25 has three treating tanks 25a through 25c. The first tank 25a is provided with pelletized soil humus 26 and crushed igneous rocks 27. The second and third tanks 25b and 25c has crushed igneous rocks 27 only. Each of the treating tanks 25a through 25c is aerated by means of aeration pipes 29a to 29c connected to the aeration unit 28. The effluent from the third tanks 25c is sent as the final product to the storage tank 30. Part of the liquid held in the storage tank 30 is recycled back to the first tank 25a. Tap water supplied to the swinery barn 20 as drinking water is pretreated in the drinking water treatment tank 30 which contains pelletized soil humus and crushed igneous rocks.

The thus constructed system, similar to the one of Example 1, facilitates the removal of offensive odor in a short time and to convert urine-based wastes into an aqueous solution rich in activated soil microorganisms and their metabolic by-products.

The aqueous solution in each system described in Examples 1 and 2 promotes the growth of crops and improves soil when being spread over farmland and other land with vegetation. Moreover, drinking water for domestic animals is improved by mixing of the liquid, thereby reducing offensive odor emitted from the urine itself. When spraying the aqueous solution diluted by water in a barn, the working environment of the barn is much improved and offensive odors can be eliminated considerably. Other advantages of the solution are, such as for example, it prevents mammillitis when sprayed over the nipples of diary cattle immediately after milking and it curtails the proliferation of harmful insects and miscellaneous bacteria. In addition, it accelerates the curing of compost from solid wastes when sprayed or added by other suitable means. These benefits can be directly attributed to the solution's high concentration of activated soil microorganisms and their metabolic by-products.

What is claimed is:

1. A method for treating liquid wastes of domestic animals consisting essentially of urine, which comprises mixing said liquid wastes with soil humus, bioreacting the mixture with aeration in the presence of igneous rocks selected from the group consisting of andesite, basalt, granite, rhyolite, and peridotite, and soil humus in order to accelerate the metabolic activities of the soil microorganisms, and extracting a liquid component containing activated soil microorganisms and their metabolic products from the mixture.

2. A method for treating liquid wastes of domestic animals consisting essentially of urine, comprising raising the domestic animals using as their drinking water water having dissolved therein useful minerals from rocks and soil microorganisms, prepared by mixing in water a plurality of igneous rocks selected from the group consisting of andesite, basalt, granite, rhyolite, and peridotite, and soil humus with aeration, collecting liquid wastes consisting essentially of urine from the domestic animals using said drinking water, and mixing with said liquid wastes consisting essentially of urine a plurality of igneous rocks selected from the group consisting of andesite, basalt, granite, rhyolite, and peridotite, and soil humus for activating the soil microorganisms and converting the mixture by bioreaction with aeration into an aqueous solution containing activated microorganisms and their metabolic by-products.

3. A method for treating liquid wastes of domestic animals as claimed in claim 2, wherein said drinking water consists essentially of water and an aqueous solution of activated microorganisms and their metabolic products produced by bioreacting urine-based excretions discharged from domestic animals in the presence of humus and rocks.

4. A method for treating liquid wastes of domestic animals as claimed in claim 2, wherein said aqueous solution is sprayed in a barn in which domestic animals are raised.

* * * * *